US006444456B1

(12) United States Patent
Walke et al.

(10) Patent No.: US 6,444,456 B1
(45) Date of Patent: Sep. 3, 2002

(54) HUMAN G-COUPLED PROTEIN RECEPTOR KINASES AND POLYNUCLEOTIDES ENCODING THE SAME

(75) Inventors: D. Wade Walke, Spring; Nathaniel L. Wilganowski, Houston; C. Alexander Turner, Jr., The Woodlands, all of TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 09/802,117

(22) Filed: Mar. 8, 2001

Related U.S. Application Data
(60) Provisional application No. 60/188,449, filed on Mar. 10, 2000.

(51) Int. Cl.[7] .......................... C12N 9/12; C12N 15/79; C12N 5/10; C07H 21/04; C12Q 1/48

(52) U.S. Cl. ....................... 435/194; 536/23.2; 435/15; 435/325; 435/252.3; 435/320.1

(58) Field of Search .......................... 536/23.2; 435/15, 435/194, 325, 252.3, 320.1

(56) References Cited

U.S. PATENT DOCUMENTS

| | | |
|---|---|---|
| 4,215,051 A | 7/1980 | Schroeder et al. |
| 4,376,110 A | 3/1983 | David et al. |
| 4,594,595 A | 6/1986 | Struckman |
| 4,631,211 A | 12/1986 | Houghten |
| 4,689,405 A | 8/1987 | Frank et al. |
| 4,713,326 A | 12/1987 | Dattagupta et al. |
| 4,946,778 A | 8/1990 | Ladner et al. |
| 5,252,743 A | 10/1993 | Barrett et al. |
| 5,424,186 A | 6/1995 | Fodor et al. |
| 5,445,934 A | 8/1995 | Fodor et al. |
| 5,459,127 A | 10/1995 | Felgner et al. |
| 5,532,151 A | 7/1996 | Chantry et al. |
| 5,556,752 A | 9/1996 | Lockhart et al. |
| 5,591,618 A | 1/1997 | Chantry et al. |
| 5,700,637 A | 12/1997 | Southern |
| 5,744,305 A | 4/1998 | Fodor et al. |
| 5,830,721 A | 11/1998 | Stemmer et al. |
| 5,837,458 A | 11/1998 | Minshull et al. |
| 5,869,336 A | 2/1999 | Meyer et al. |
| 5,877,397 A | 3/1999 | Lonberg et al. |
| 5,948,767 A | 9/1999 | Scheule et al. |
| 6,075,181 A | 6/2000 | Kucherlapati et al. |
| 6,110,490 A | 8/2000 | Thierry |
| 6,150,584 A | 11/2000 | Kucherlapati et al. |
| 6,331,423 B1 * | 12/2001 | Guegler et al. ............. 435/194 |

FOREIGN PATENT DOCUMENTS

WO     WO 01/38503 A2    5/2001

OTHER PUBLICATIONS

Broun et al., Science 282:1315–1317, 1998.*
Van de Loo et al., Proc. Natl. Acad. Sci. 92:6743–6747, 1995.*
Weiss et al., GenEMBL accession No. AF063016, Dec. 1998.*
Weiss et al., SPTREMBL accession No. Q9Z2G7, May 1999.*
Database EMBL (Online) May 7, 2000, Birren, B. et al. "Homo sapiens chromosome 17, clone RP11–144C9", Database accession No. AC068693, XP002181811.
Weiss, Ellen R. et al., "The cloning of GRK7, a candidate cone opsin kinase, from cone and rod–dominant mammalian retinas," Molecular Vison, vol. 4, Dec. 8, 1998, p. 27, XP002181808.
Premont, Richard T. et al., "The GRK4 subfamily o9f G protein–coupled receptor kinases: Alternative splicing, gene organization, and sequence conservation," Journal of Biological Chemistry, vol. 274, No. 41, Oct. 8, 1999, pp. 29381–29389, XP002181809.
Benovic, Jeffrey L. et al., "Molecular cloning and expression of GRK6: A new member of the G protein–coupled receptor kinase family," Journal of Biological Chemistry, vol. 268, No. 26, 1993, pp. 19521–19527, XP002181810.
International Search Report, International Application No. PCT/US01/07500, Nov. 8, 2001.
Bird et al, 1988, "Single–Chain Antigen–Binding Proteins", Science 242:423–426.
Bitter et al, 1987, "Expression and Secretion Vectors for Yeast", Methods in Enzymology 153:516–544.
Colbere–Garapin et al, 1981, "A New Dominant Hybrid Selective Marker for Higher Eukaryotic Cells", J. Mol. Biol. 150:1–14.
Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.
Greenspan et al, 1993, "Idiotypes: structure and immunogenicity", FASEB Journal 7:437–444.
Huse et al, 1989, "Generation of a Large Combinatorial Library of the Immunoglobulin Repertoire in Phage Lambda", Science 246:1275–1281.
Huston et al, 1988, "Protein engineering of antibody binding sites: Recovery of specific activity in an anti–digoxin single–chain Fv analogue produced in *escherichia coli*", Proc. Natl. Acad. Sci. USA 85:5879–5883.
Inoue et al, 1987, "Sequence–dependent hydrolysis of RNA using modified oligonucleotide splints and R Nase H", FEBS Letters 215(2):327–330.

(List continued on next page.)

*Primary Examiner*—Ponnathapu Achutamurthy
*Assistant Examiner*—Delia Ramirez

(57) ABSTRACT

Novel human polynucleotide and polypeptide sequences are disclosed that can be used in therapeutic, diagnostic, and pharmacogenomic applications.

4 Claims, No Drawings

OTHER PUBLICATIONS

Inoue et al, 1987, "Synthesis and hybridization studies on two complementary nona(2'–O–methyl)ribonucleotides", Nucleic Acids Research 15(15):6131–6149.

Inouye & Inouye, 1985, "Up–promoter mutations in the lpp gene of *Escherichia coli*", Nucleic Acids Research 13(9):3101–3110.

Janknecht et al, 1991, "Rapid and efficient purification of native histidine–tagged protein expressed by recombinant vaccinia virus", PNAS 88:8972–8976.

Kohler & Milstein, 1975, "Continuous cultures of fused cells secreting antibody of predefined specificity", Nature 256:495–497.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the Autographa californica Nuclear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

* cited by examiner

SEQUENCE LISTING

<160> NUMBER OF SEQ ID NOS: 5

<210> SEQ ID NO 1
<211> LENGTH: 1662
<212> TYPE: DNA
<213> ORGANISM: homo sapiens

<400> SEQUENCE: 1

| | | | | | |
|---|---|---|---|---|---|
| atggtggaca | tgggggccct | ggayaacctg | atcgccaaca | ccgcctacct | gcaggcccgg | 60 |
| aagccctcgg | actgcgacag | caaagagctg | cagcggcggc | ggcgtagcct | ggccctgccc | 120 |
| gggctgcagg | gctgcgcgga | gctccgccag | aagctgtccc | tgaacttcca | cagcctgtgt | 180 |
| gagcagcagc | ccatcggtcg | ccgcctcttc | cgtgacttcc | tagccacagt | gcccacgttc | 240 |
| cgcaaggcgg | caaccttcct | agaggacgtg | cagaactggg | agctggccga | ggagggaccc | 300 |
| accaaagaca | gcgcgctgca | ggggctggtg | gccacttgtg | cgagtgcccc | tgccccgggg | 360 |
| aacccgcaac | ccttcctcag | ccaggccgtg | gccaccaagt | gccaagcagc | caccactgag | 420 |
| gaagagcgag | tggctgcagt | gacgctggcc | aaggctgagg | ccatggcttt | cttgcaagag | 480 |
| cagccctta | aggatttcgt | gaccagcgcc | ttctacgaca | agtttctgca | gtggaaactc | 540 |
| ttcgagatgc | aaccagtgtc | agacaagtac | ttcactgagt | tcagagtgct | ggggaaaggt | 600 |
| ggttttgggg | aggtatgtgc | cgtccaggtg | aaaaacactg | ggaagatgta | tgcctgtaag | 660 |
| aaactggaca | agaagcggct | gaagaagaaa | ggtggcgaga | agatggctct | cttggaaaag | 720 |
| gaaatcttgg | agaaggtcag | cagcccttc | attgtctctc | tggcctatgc | ctttgagagc | 780 |
| aagacccatc | tctgccttgt | catgagcctg | atgaatgggg | agacctcaa | gttccacatc | 840 |
| tacaacgtgg | gcacgcgtgg | cctggacatg | agccgggtga | tcttttactc | ggcccagata | 900 |
| gcctgtggga | tgctgcacct | ccatgaactc | ggcatcgtct | atcgggacat | gaagcctgag | 960 |
| aatgtgcttc | tggatgacct | cggcaactgc | aggttatctg | acctggggct | ggccgtggag | 1020 |
| atgaagggtg | gcaagcccat | cacccagagg | gctggaacca | atggttacat | ggctcctgag | 1080 |
| atcctaatgg | aaaaggtaag | ttattcctat | cctgtggact | ggtttgccat | gggatgcagc | 1140 |
| atttatgaaa | tggttgctgg | acgaacacca | ttcaaagatt | acaaggaaaa | ggtcagtaaa | 1200 |
| gaggatctga | agcaaagaac | tctgcaagac | gaggtcaaat | tccagcatga | taacttcaca | 1260 |
| gaggaagcaa | aagatatttg | caggctcttc | ttggctaaga | aaccagagca | acgcttagga | 1320 |
| agcagagaaa | agtctgatga | tcccaggaaa | catcatttct | ttaaaacgat | caactttcct | 1380 |
| cgcctggaag | ctggcctaat | tgaaccccca | tttgtgccag | accttcagt | ggtttatgcc | 1440 |
| aaagacatcg | ctgaaattga | tgatttctct | gaggttcggg | gggtggaatt | tgatgacaaa | 1500 |

-continued

```
gataagcagt tcttcaaaaa ctttgcgaca ggtgctgttc ctatagcatg gcaggaagaa      1560
attatagaaa cgggactgtt tgaggaactg aatgacccca acagacctac ggttgtgag       1620 gagggtaatt catccaagtc tggcgtgtgt ttgttattgt aa                         1662
```

<210> SEQ ID NO 2
<211> LENGTH: 553
<212> TYPE: PRT
<213> ORGANISM: homo sapiens

<400> SEQUENCE: 2

```
Met Val Asp Met Gly Ala Leu Asp Asn Leu Ile Ala Asn Thr Ala Tyr
 1               5                  10                  15

Leu Gln Ala Arg Lys Pro Ser Asp Cys Asp Ser Lys Glu Leu Gln Arg
            20                  25                  30

Arg Arg Arg Ser Leu Ala Leu Pro Gly Leu Gln Gly Cys Ala Glu Leu
        35                  40                  45

Arg Gln Lys Leu Ser Leu Asn Phe His Ser Leu Cys Glu Gln Gln Pro
    50                  55                  60

Ile Gly Arg Arg Leu Phe Arg Asp Phe Leu Ala Thr Val Pro Thr Phe
65                  70                  75                  80

Arg Lys Ala Ala Thr Phe Leu Glu Asp Val Gln Asn Trp Glu Leu Ala
                85                  90                  95

Glu Glu Gly Pro Thr Lys Asp Ser Ala Leu Gln Gly Leu Val Ala Thr
            100                 105                 110

Cys Ala Ser Ala Pro Ala Pro Gly Asn Pro Gln Pro Phe Leu Ser Gln
        115                 120                 125

Ala Val Ala Thr Lys Cys Gln Ala Ala Thr Thr Glu Glu Glu Arg Val
    130                 135                 140

Ala Ala Val Thr Leu Ala Lys Ala Glu Ala Met Ala Phe Leu Gln Glu
145                 150                 155                 160

Gln Pro Phe Lys Asp Phe Val Thr Ser Ala Phe Tyr Asp Lys Phe Leu
                165                 170                 175

Gln Trp Lys Leu Phe Glu Met Gln Pro Val Ser Asp Lys Tyr Phe Thr
            180                 185                 190

Glu Phe Arg Val Leu Gly Lys Gly Phe Gly Glu Val Cys Ala Val
        195                 200                 205

Gln Val Lys Asn Thr Gly Lys Met Tyr Ala Cys Lys Lys Leu Asp Lys
    210                 215                 220

Lys Arg Leu Lys Lys Gly Gly Glu Lys Met Ala Leu Leu Glu Lys
225                 230                 235                 240

Glu Ile Leu Glu Lys Val Ser Ser Pro Phe Ile Val Ser Leu Ala Tyr
                245                 250                 255

Ala Phe Glu Ser Lys Thr His Leu Cys Leu Val Met Ser Leu Met Asn
            260                 265                 270

Gly Gly Asp Leu Lys Phe His Ile Tyr Asn Val Gly Thr Arg Gly Leu
        275                 280                 285

Asp Met Ser Arg Val Ile Phe Tyr Ser Ala Gln Ile Ala Cys Gly Met
    290                 295                 300

Leu His Leu His Glu Leu Gly Ile Val Tyr Arg Asp Met Lys Pro Glu
305                 310                 315                 320

Asn Val Leu Leu Asp Asp Leu Gly Asn Cys Arg Leu Ser Asp Leu Gly
                325                 330                 335

Leu Ala Val Glu Met Lys Gly Gly Lys Pro Ile Thr Gln Arg Ala Gly
```

```
                    340           345           350
Thr Asn Gly Tyr Met Ala Pro Glu Ile Leu Met Glu Lys Val Ser Tyr
            355                 360                 365
Ser Tyr Pro Val Asp Trp Phe Ala Met Gly Cys Ser Ile Tyr Glu Met
        370                 375                 380
Val Ala Gly Arg Thr Pro Phe Lys Asp Tyr Lys Glu Lys Val Ser Lys
385                 390                 395                 400
Glu Asp Leu Lys Gln Arg Thr Leu Gln Asp Glu Val Lys Phe Gln His
                405                 410                 415
Asp Asn Phe Thr Glu Glu Ala Lys Asp Ile Cys Arg Leu Phe Leu Ala
                420                 425                 430
Lys Lys Pro Glu Gln Arg Leu Gly Ser Arg Glu Lys Ser Asp Asp Pro
            435                 440                 445
Arg Lys His His Phe Phe Lys Thr Ile Asn Phe Pro Arg Leu Glu Ala
        450                 455                 460
Gly Leu Ile Glu Pro Pro Phe Val Pro Asp Pro Ser Val Val Tyr Ala
465                 470                 475                 480
Lys Asp Ile Ala Glu Ile Asp Asp Phe Ser Glu Val Arg Gly Val Glu
                485                 490                 495
Phe Asp Asp Lys Asp Lys Gln Phe Phe Lys Asn Phe Ala Thr Gly Ala
                500                 505                 510
Val Pro Ile Ala Trp Gln Glu Ile Ile Glu Thr Gly Leu Phe Glu
            515                 520                 525
Glu Leu Asn Asp Pro Asn Arg Pro Thr Gly Cys Glu Glu Gly Asn Ser
        530                 535                 540
Ser Lys Ser Gly Val Cys Leu Leu Leu
545                 550
```

<210> SEQ ID NO 3
<211> LENGTH: 1062
<212> TYPE: DNA
<213> ORGANISM: homo sapiens

<400> SEQUENCE: 3

```
atggtggaca tggggggccct ggacaacctg atcgccaaca ccgcctacct gcaggcccgg      60
aagccctcgg actgcgacag caaagagctg cagcggcggc ggcgtagcct ggccctgccc     120
gggctgcagg gctgcgcgga gctccgccag aagctgtccc tgaacttcca cagcctgtgt     180
gagcagcagc ccatcggtcg ccgcctcttc cgtgacttcc tagccacagt gcccacgttc     240
cgcaaggcgg caaccttcct agaggacgtg cagaactggg agctggccga ggagggaccc     300
accaaagaca gcgcgctgca ggggctggtg gccacttgtg cgagtgcccc tgccccgggg     360
aacccgcaac ccttcctcag ccaggccgtg gccaccaagt gccaagcagc caccactgag     420
gaagagcgag tggctgcagt gacgctggcc aaggctgagg ccatggcttt cttgcaagag     480
cagccccttta aggatttcgt gaccagcgcc ttctacgaca gtttctgca gtggaaactc     540
ttcgagatgc aaccagtgtc agacaagtac ttcactgagt tcagagtgct ggggaaaggt     600
ggttttgggg aggtatgtgc cgtccaggtg aaaaacactg gaagatgta tgcctgtaag     660
aaactggaca gaagcggct gaagaagaaa ggtggcgaga gatggctct cttggaaaag     720
gaaatcttgg agaaggtcag cagcccttc attgtctctc tggcctatgc ctttgagagc     780
aagacccatc tctgccttgt catgagcctg atgaatgggg agacctcaa gttccacatc     840
tacaacgtgg gcacgcgtgg cctggacatg agccgggtga tcttttactc ggcccagata     900
```

```
gcctgtggga tgctgcacct ccatgaactc ggcatcgtct atcgggacat gaagcctgag    960
aatgtgcttc tggatgacct cggcaactgc aggttatctg acctggggct ggccgtggag   1020
atgaagggtg caagcccat cacccagagg agaaaagtct ga                       1062
```

<210> SEQ ID NO 4
<211> LENGTH: 353
<212> TYPE: PRT
<213> ORGANISM: homo sapiens

<400> SEQUENCE: 4

```
Met Val Asp Met Gly Ala Leu Asp Asn Leu Ile Ala Asn Thr Ala Tyr
 1               5                  10                  15

Leu Gln Ala Arg Lys Pro Ser Asp Cys Asp Ser Lys Glu Leu Gln Arg
            20                  25                  30

Arg Arg Arg Ser Leu Ala Leu Pro Gly Leu Gln Gly Cys Ala Glu Leu
        35                  40                  45

Arg Gln Lys Leu Ser Leu Asn Phe His Ser Leu Cys Glu Gln Gln Pro
    50                  55                  60

Ile Gly Arg Arg Leu Phe Arg Asp Phe Leu Ala Thr Val Pro Thr Phe
65                  70                  75                  80

Arg Lys Ala Ala Thr Phe Leu Glu Asp Val Gln Asn Trp Glu Leu Ala
                85                  90                  95

Glu Glu Gly Pro Thr Lys Asp Ser Ala Leu Gln Gly Leu Val Ala Thr
           100                 105                 110

Cys Ala Ser Ala Pro Ala Pro Gly Asn Pro Gln Pro Phe Leu Ser Gln
       115                 120                 125

Ala Val Ala Thr Lys Cys Gln Ala Ala Thr Thr Glu Glu Glu Arg Val
   130                 135                 140

Ala Ala Val Thr Leu Ala Lys Ala Glu Ala Met Ala Phe Leu Gln Glu
145                 150                 155                 160

Gln Pro Phe Lys Asp Phe Val Thr Ser Ala Phe Tyr Asp Lys Phe Leu
               165                 170                 175

Gln Trp Lys Leu Phe Glu Met Gln Pro Val Ser Asp Lys Tyr Phe Thr
           180                 185                 190

Glu Phe Arg Val Leu Gly Lys Gly Gly Phe Gly Glu Val Cys Ala Val
       195                 200                 205

Gln Val Lys Asn Thr Gly Lys Met Tyr Ala Cys Lys Lys Leu Asp Lys
   210                 215                 220

Lys Arg Leu Lys Lys Lys Gly Gly Glu Lys Met Ala Leu Leu Glu Lys
225                 230                 235                 240

Glu Ile Leu Glu Lys Val Ser Ser Pro Phe Ile Val Ser Leu Ala Tyr
               245                 250                 255

Ala Phe Glu Ser Lys Thr His Leu Cys Leu Val Met Ser Leu Met Asn
           260                 265                 270

Gly Gly Asp Leu Lys Phe His Ile Tyr Asn Val Gly Thr Arg Gly Leu
       275                 280                 285

Asp Met Ser Arg Val Ile Phe Tyr Ser Ala Gln Ile Ala Cys Gly Met
   290                 295                 300

Leu His Leu His Glu Leu Gly Ile Val Tyr Arg Asp Met Lys Pro Glu
305                 310                 315                 320

Asn Val Leu Leu Asp Asp Leu Gly Asn Cys Arg Leu Ser Asp Leu Gly
               325                 330                 335

Leu Ala Val Glu Met Lys Gly Gly Lys Pro Ile Thr Gln Arg Arg Lys
           340                 345                 350
```

Val

<210> SEQ ID NO 5
<211> LENGTH: 2249
<212> TYPE: DNA
<213> ORGANISM: homo sapiens

<400> SEQUENCE: 5

| | | | | | | |
|---|---|---|---|---|---|---|
| aaaactgctc | tgaggccatc | atgctttgag | gaagcccagg | aggaaacact | gcagagaggc | 60 |
| tcaaccaccc | cagctctccc | agctgagctc | agccacccac | cgatccccca | gctgaatgca | 120 |
| accataagag | tgagtccagg | ttctaccctg | ctaggctgcc | accacattcc | taagaaccac | 180 |
| gggaaaaggc | atttgctcct | ccgaagaaat | tctcagactg | attttcact | gtattgtcag | 240 |
| gccacaggac | tcactgtaaa | tcccttggac | gttgtctcac | ccgggaaggg | aaagcagcca | 300 |
| gcagccctcc | agcctcttg | tgctttccct | gggagtgcgc | cccgtgctca | gccatggtgg | 360 |
| acatggggc | cctggacaac | ctgatcgcca | acaccgccta | cctgcaggcc | cggaagccct | 420 |
| cggactgcga | cagcaaagag | ctgcagcggg | gcggcgtag | cctggccctg | cccgggctgc | 480 |
| agggctgcgc | ggagctccgc | cagaagctgt | ccctgaactt | ccacagcctg | tgtgagcagc | 540 |
| agcccatcgg | tcgccgcctc | ttccgtgact | tcctagccac | agtgcccacg | ttccgcaagg | 600 |
| cggcaacctt | cctagaggac | gtgcagaact | gggagctggc | cgaggaggga | cccaccaaag | 660 |
| acagcgcgct | gcaggggctg | gtggccactt | gtgcgagtgc | ccctgccccg | gggaacccgc | 720 |
| aaccccttcct | cagccaggcc | gtggccacca | agtgccaagc | agccaccact | gaggaagagc | 780 |
| gagtggctgc | agtgacgctg | gccaaggctg | aggccatggc | tttcttgcaa | gagcagccct | 840 |
| ttaaggattt | cgtgaccagc | gccttctacg | acaagtttct | gcagtggaaa | ctcttcgaga | 900 |
| tgcaaccagt | gtcagacaag | tacttcactg | agttcagagt | gctggggaaa | ggtggttttg | 960 |
| ggaggtatg | tgccgtccag | gtgaaaaaca | ctgggaagat | gtatgcctgt | aagaaactgg | 1020 |
| acaagaagcg | gctgaagaag | aaaggtggcg | agaagatggc | tctcttggaa | aaggaaatct | 1080 |
| ggagaaggt | cagcagccct | ttcattgtct | ctctggccta | tgcctttgag | agcaagaccc | 1140 |
| atctctgcct | tgtcatgagc | ctgatgaatg | ggggagacct | caagttccac | atctacaacg | 1200 |
| tgggcacgcg | tggcctggac | atgagccggg | tgatctttta | ctcggcccag | atagcctgtg | 1260 |
| ggatgctgca | cctccatgaa | ctcggcatcg | tctatcggga | catgaagcct | gagaatgtgc | 1320 |
| ttctggatga | cctcggcaac | tgcaggttat | ctgacctggg | gctggccgtg | gagatgaagg | 1380 |
| gtggcaagcc | catcacccag | agggctggaa | ccaatggtta | catggctcct | gagatcctaa | 1440 |
| tggaaaaggt | aagttattcc | tatcctgtgg | actggtttgc | catgggatgc | agcatttatg | 1500 |
| aaatggttgc | tggacgaaca | ccattcaaag | attacaagga | aaggtcagt | aaagaggatc | 1560 |
| tgaagcaaag | aactctgcaa | gacgaggtca | attccagca | tgataacttc | acagaggaag | 1620 |
| caaaagatat | ttgcaggctc | ttcttggcta | agaaaccaga | gcaacgctta | ggaagcagag | 1680 |
| aaaagtctga | tgatcccagg | aaacatcatt | tctttaaaac | gatcaacttt | cctcgcctgg | 1740 |
| aagctggcct | aattgaaccc | ccatttgtgc | cagaccccttc | agtggtttat | gccaaagaca | 1800 |
| tcgctgaaat | tgatgatttc | tctgaggttc | gggggtgga | atttgatgac | aaagataagc | 1860 |
| agttcttcaa | aaactttgcg | acaggtgctg | ttcctatagc | atggcaggaa | gaaattatag | 1920 |
| aaacgggact | gtttgaggaa | ctgaatgacc | caacagacc | tacgggttgt | gaggagggta | 1980 |
| attcatccaa | gtctggcgtg | tgtttgttat | tgtaaattgc | tctctttacc | agacaggcag | 2040 |

| | | | | |
|---|---|---|---|---|
| caggagtctc | ggctgacata | atcctcgaat | gttccacacg | tggaaatctg tggaatgagg | 2100 |
| gctaatcagt | taggagggac | atcacaacca | caaaacaatt | caaaagacag gcaagctcac | 2160 |
| tactagaaca | cattttattt | tcttttctt | tcttcataaa | gatgagtaaa gtctcagttt | 2220 |
| tcactgaggg | cagggaaaag | gaacactca | | | 2249 |

HUMAN G-COUPLED PROTEIN RECEPTOR KINASES AND POLYNUCLEOTIDES ENCODING THE SAME

The present application claims the benefit of U.S. Provisional Application No. 60/188,449 which was filed on Mar. 10, 2000 and is herein incorporated by reference in its entirety.

1. INTRODUCTION

The present invention relates to the discovery, identification, and characterization of novel human polynucleotides encoding proteins that share sequence similarity with animal kinases. The invention encompasses the described polynucleotides, host cell expression systems, the encoded proteins, fusion proteins, polypeptides and peptides, antibodies to the encoded proteins and peptides, and genetically engineered animals that either lack or over express the disclosed polynucleotides, antagonists and agonists of the proteins, and other compounds that modulate the expression or activity of the proteins encoded by the disclosed polynucleotides that can be used for diagnosis, drug screening, clinical trial monitoring and the treatment of diseases and physiological disorders.

2. BACKGROUND OF THE INVENTION

Kinases mediate phosphorylation of a wide variety of proteins and compounds in the cell. In conjunction with phosphatases, kinases are involved in a range of regulatory and signaling pathways. Given the physiological importance of kinases, they have been subject to intense scrutiny and are proven drug targets.

3. SUMMARY OF THE INVENTION

The present invention relates to the discovery, identification, and characterization of nucleotides that encode novel human proteins and the corresponding amino acid sequences of these proteins. The novel human proteins (NHPs) described for the first time herein share structural similarity with animal kinases, including, but not limited to G-protein coupled receptor kinases (GRKs). As such, the novel polynucleotides encode novel GRKs having homologues and orthologs across a range of phyla and species.

The novel human polynucleotides described herein, encode open reading frames (ORFs) encoding proteins of 553 and 353 amino acids in length (see SEQ ID NOS:2 and 4 respectively).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP polynucleotides (e.g., expression constructs that place the described polynucleotide under the control of a strong promoter system), and transgenic animals that express a NHP transgene, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–5 are "knocked-out" they provide a method of identifying phenotypic expression of the particular gene as well as a method of assigning function to previously unknown genes. Additionally, the unique NHP sequences described in SEQ ID NOS:1–5 are useful for the identification of coding sequence and the mapping a unique gene to a particular chromosome.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances

4. DESCRIPTION OF THE SEQUENCE LISTING AND FIGURES

The Sequence Listing provides the sequence of the novel human ORFs encoding the described novel human kinase proteins. SEQ ID NO:5 describes a full length ORF and flanking regions.

5. DETAILED DESCRIPTION OF THE INVENTION

The NHPs, described for the first time herein, are novel proteins that are expressed in, inter alia, human cell lines, and human fetal brain, adult brain, pituitary, cerebellum, spinal cord, thymus, kidney, fetal liver, prostate, testis, adrenal gland, small intestine, skeletal muscle, uterus, placenta, mammary gland, and pericardium cells. The described sequences were compiled from gene trapped sequences in conjunction with sequences available in GENBANK, and cDNAs from adrenal gland, skeletal muscle, thymus, and testis libraries (Edge Biosystems, Gaithersburg, Md.).

The present invention encompasses the nucleotides presented in the Sequence Listing, host cells expressing such nucleotides, the expression products of such nucleotides, and: (a) nucleotides that encode mammalian homologs of the described polynucleotides, including the specifically described NHPs, and the NHP products; (b) nucleotides that encode one or more portions of an NHP that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor/ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing. As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1× SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequence that encode and express an amino acid sequence presented in the Sequence Listing under moderately stringent conditions, e.g., washing in 0.2× SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar to corresponding regions of SEQ ID NO:1 (as measured by BLAST sequence comparison analysis using, for example, the GCG sequence analysis package using default parameters).

The invention also includes nucleic acid molecules, preferably DNA molecules, that hybridize to, and are therefore the complements of, the described NHP encoding polynucleotides. Such hybridization conditions can be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–5 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–5, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–5 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–5.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–5 provides detailed information about transcriptional changes involved in a specific pathway, potentially leading to the identification of novel components or gene functions that manifest themselves as novel phenotypes.

Probes consisting of sequences first disclosed in SEQ ID NOS:1–5 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–5 can be utilized in microarrays or other assay formats, to screen collections of genetic material from patients who have a particular medical condition. These investigations can also be carried out using the sequences first disclosed in SEQ ID NOS:1–5 in silico and by comparing previously collected genetic databases and the disclosed sequences using computer software known to those in the art.

Thus the sequences first disclosed in SEQ ID NOS:1–5 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–5. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relatve to one or more additional sequence(s) or one or more restriction sites present in the disclosed sequence.

For oligonucleotide probes, highly stringent conditions may refer, e.g., to washing in 6× SSC/0.05% sodium pyrophosphate at 37° C. (for 14-base oligos), 48° C. (for 17-base oligos)., 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences can be used as part of ribozyme and/or triple helix sequences that are also useful for NHP gene regulation, or as NHP regulating aptamers.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from, for example, human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, immune disorders, obesity, high blood pressure, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue may be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor, N.Y.)

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

Where, as in the present instance, some of the described NHP peptides or polypeptides are thought to be cytoplasmic proteins, expression systems can be engineered that produce soluble derivatives of a NHP (corresponding to a NHP extracellular and/or intracellular domains, or truncated polypeptides lacking one or more hydrophobic domains) and/or NHP fusion protein products (especially NHP-Ig fusion proteins, i.e., fusions of a NHP domain to an IgFc), NHP antibodies, and anti-idiotypic antibodies (including Fab fragments) that can be used in therapeutic applications. Preferably, the above expression systems are engineered to allow the desired peptide or polypeptide to be recovered from the culture media.

The present invention also encompasses antibodies and anti-idiotypic antibodies (including Fab fragments), antagonists and agonists of a NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHP in the body. The use of engineered host cells and/or animals can offer an advantage in that such systems allow not only for the identification of compounds that bind to the endogenous receptor/ligand of a NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP or a protein interactive therewith. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and corresponding deduced amino acid sequences of the described NHPs are presented in the Sequence Listing.

Expression analysis has provided evidence that the described NHPs can be expressed in human tissues as well as gene trapped human cells. In addition to GRKs, the described NHPs share significant similarity to a range of kinase families from a variety of phyla and species. Similar polynucleotides encoding GRK proteins, as well as uses and applications that are germane to the described NHPs are described in U.S. Pat. Nos. 5,591,618 and 5,532,151 which are herein incorporated by reference in their entirety.

5.2 NHPS and NHP Polypeptides

NHP products, polypeptides, peptide fragments, mutated, truncated, or deleted forms of the NHPs, and/or NHP fusion proteins can be prepared for a variety of uses. These uses include, but are not limited to, the generation of antibodies, as reagents in diagnostic assays, the identification of other cellular gene products related to the NHP, as reagents in assays for screening for compounds that can be used as pharmaceutical reagents useful in the therapeutic treatment of mental, biological, or medical disorders and disease.

The Sequence Listing discloses the amino acid sequences encoded by the described NHP-encoding polynucleotides. The NHPs display initiator methionines in a DNA sequence context consistent with eucaryotic translation initiation site, and a weak signal sequence characteristic of membrane associated proteins.

The NHP amino acid sequences of the invention include the amino acid sequences presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and modify a NHP substrate, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by a NHP nucleotide sequence described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where the NHP peptide or polypeptide can exist, or has been engineered to exist, as a soluble or secreted molecule, the soluble NHP peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., E. coli, B. subtilis) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3)

harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited to, the E. coli expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, Autographa californica nuclear polyhidrosis virus (AcNPV) is used as a vector to express foreign polynucleotides. The virus grows in Spodoptera frugiperda cells. A NHP encoding polynucleotide sequence can be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted polynucleotide is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems can be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the polynucleotide of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in *Liposomes: A Practical Approach*, New, RRC ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ, where they cross the cell membrane and/or the nucleus where the NHP can exert its functional activity. This goal may be achieved by coupling of the NHP to a cytokine or other ligand that provides targeting specificity, and/or to a protein transducing domain (see generally U.S. application Ser. No. 60/111,701 and 60/056,713, both of which are herein incorporated by reference, for examples of such transducing sequences) to facilitate passage across cellular membranes and can optionally be engineered to include nuclear localization sequences.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention can be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, a NHP peptide (e.g., one corresponding to a functional domain of a NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mabs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150, 584 and respective disclosures which are herein incorporated by reference in their entirety.

Alternatively, techniques described for the production of single chain antibodies (U.S. Pat. No. 4,946,778; Bird, 1988, Science 242:423–426;Huston et al., 1988, Proc. Natl. Acad. Sci. USA 85:5879–5883; and Ward et al., 1989, Nature 341:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor/ligand can be used to generate anti-idiotypes that "mimic" the NHP and, therefore, bind, activate, or neutralize a NHP, NHP receptor, or NHP ligand. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising the nucleotide sequence disclosed in SEQ ID NO: 1.

2. An isolated nucleic acid molecule comprising a nucleotide sequence that:
   (a) encodes the amino acid sequence shown in SEQ ID NO: 2; and
   (b) hybridizes under highly stringent conditions to the polynucleotide sequence of SEQ ID NO: 1 or the complete complement thereof.

3. An isolated nucleic acid molecule comprising a nucleotide sequence encoding the amino acid sequence shown in SEQ ID NO:2.

4. An isolated nucleic acid molecule comprising a nucleotide sequence encoding the amino acid sequence shown in SEQ ID NO:4.

* * * * *